US00PP33602P2

(12) United States Plant Patent
Ault

(10) Patent No.: US PP33,602 P2
(45) Date of Patent: Nov. 2, 2021

(54) ***VERNONIA* PLANT NAMED 'SUMMER'S END'**

(50) Latin Name: ***Vernonia* hybrid**
Varietal Denomination: Summer's End

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 17/132,211

(22) Filed: Dec. 23, 2020

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Vernonia* plant named 'Summer's End' that is characterized by its bushy upright plant habit with stems that do not lodge, its tolerance to high pH (alkaline) soils, its foliage that is olive green in color with no red or purple tints when grown in full sun, its high resistance to rust and powdery mildew, its hardiness in U.S.D.A. Zones 4 to 8, and its drought tolerance.

2 Drawing Sheets

Botanical classification: *Vernonia* hybrid.
Variety denomination: 'Summer's End'.

BACKGROUND OF THE INVENTION

The present invention relates to a new and distinct cultivar of *Vernonia* plant of hybrid origin and will be referred to hereinafter by its cultivar name, 'Summer's End'. The new cultivar represents a new herbaceous perennial grown for landscape use.

The new invention arose from an ongoing breeding program by the Inventor in Glencoe, Ill. The objectives of the breeding program are to develop improved cultivars of interspecific hybrids of *Vernonia* with novel ornamental traits such as plant morphologies (especially leaf and capitula size), reduced overall plant habits, improved disease resistance, hardiness in U.S.D.A. Zone 5 and in ground cultural adaptability.

'Summer's End' was derived from a cross made in September of 2012 under controlled conditions between *Vernonia lettermannii* 'Iron Butterfly' (not patented) as the female seed parent and an unnamed and unpatented plant of *Vernonia larseniae* as the male pollen parent. 'Summer's End' was selected in October of 2015 as a single unique plant amongst the resulting seedlings.

Asexual propagation of the new cultivar was first accomplished by shoot tip cuttings by the Inventor in June of 2016 in Glencoe, Ill. Asexual propagation by shoot tip and subterminal cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Summer's End' as a new and unique cultivar of *Vernonia*.

1. 'Summer's End' exhibits a bushy upright plant habit with stems that do not lodge.
2. 'Summer's End' exhibits a tolerance to high pH (alkaline) soils.
3. 'Summer's End' exhibits foliage that is olive green in color with no red or purple tints when grown in full sun.
4. 'Summer's End' exhibits a high resistance to rust (*Coleosporium* sp.) and powdery mildew (*Golovinomyces* sp.).
5. 'Summer's End' exhibits hardiness in U.S.D.A. Zones 4 to 8.
6. 'Summer's End' exhibits drought tolerance.

The female parent, 'Iron Butterfly', differs from 'Summer's End' in having a plant size that is much shorter in height, about half the number of florets per capitulum, stems and foliage that is tinted red in color when exposure to full sun, and foliage that is finer. The male parent, an unnamed plant of *Vernonia larseniae*, differs from 'Summer's End' in having phyllaries that are silvery white in color, strongly adpressed to the capitula with blunt to slightly rounded tips, foliage that is silver-white and covered with very dense pubescence, many more florets per capitulum, and in not being reliably hardy in U.S.D.A. Zone 5. 'Summer's End' can also be compared to the *Vernonia* cultivars 'Summer's Surrender' (U.S. Plant Pat. No. 28,475) and 'Summer's Swan Song' (U.S. Plant Pat. No. 28,556). 'Summer's Surrender' and 'Summer's Swan Song' are both similar to 'Summer's End' in having many upright stems that do not lodge and in having high resistance to powdery mildew and rust. 'Summer's Surrender' differs from 'Summer's End' in having more florets per capitulum, a smaller plant height and width, foliage that is longer in length, and a shorter blooming period. 'Summer's Swan Song' differs from 'Summer's End' in having a shorter plant height when mature, foliage that becomes tinted red-purple in color in full sun, more florets per capitulum, and phyllaries that are strongly adpressed to the capitula and have blunt to slightly rounded tips.

BRIEF DESCRIPTION OF THE DRAWINGS

The accompanying colored photographs illustrate the overall appearance and distinct characteristics of the new *Vernonia*. The photographs were taken of 'Summer's End' as grown in a trial garden in Glencoe, Ill.

The photograph in FIG. 1 provides a side view of a five-year-old plant of 'Summer's End' in bloom.

Figure 1:
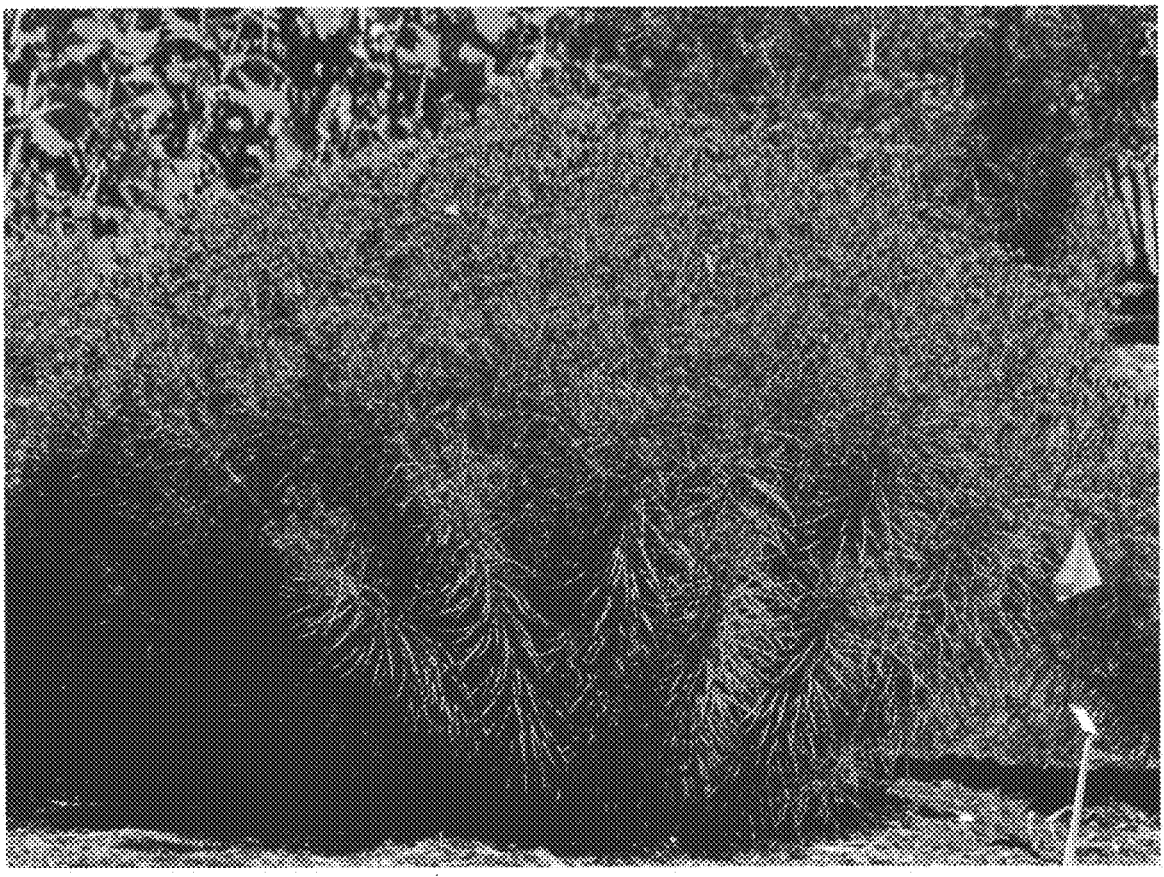
Figure 2:
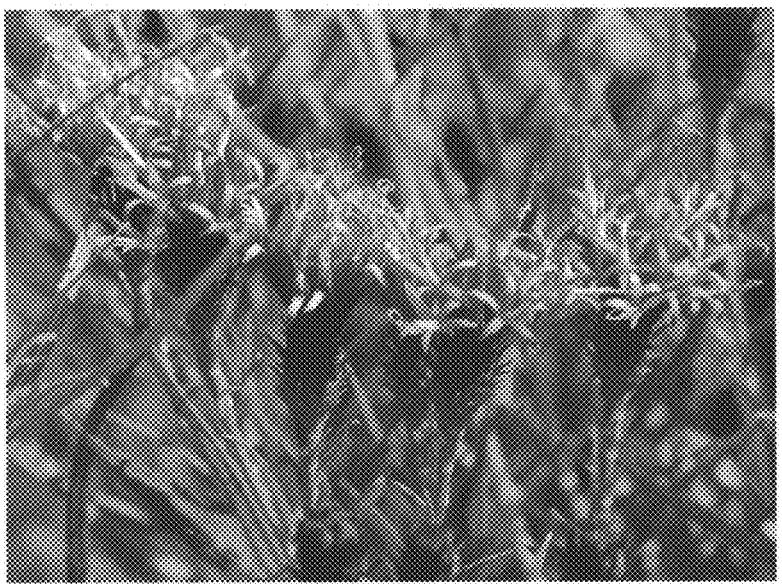

The photograph in FIG. 2 provides a close-up view of the flowers of a five-year-old plant of 'Summer's End'.

Figure 3:
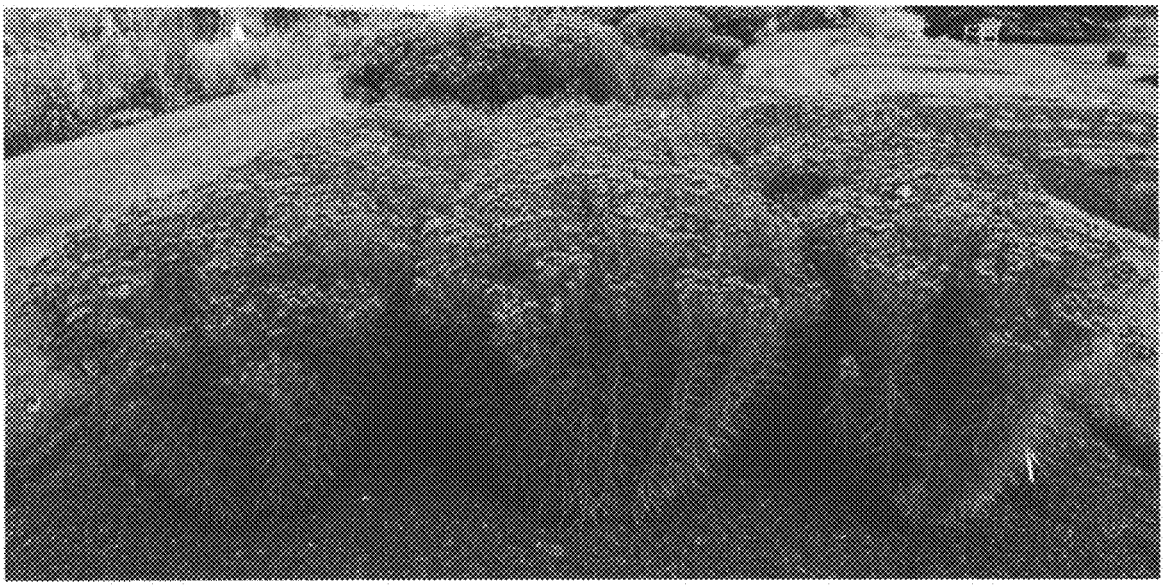

The photograph in FIG. 3 provides a view of a group of three-year-old plants of 'Summer's End'.

The colors in the photographs are as close as possible with the photographic and printing technology utilized and the color values cited in the Detailed Botanical Description accurately describe the colors of the new *Vernonia*.

DETAILED BOTANICAL DESCRIPTION

The following is a detailed description collected from two-year-old plants of the new cultivar as grown outdoors over summer in one-gallon containers, and from three to five-year-old plants grown in-ground in Glencoe, Ill. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Six weeks from early September to mid-October in northern Illinois.

*Plant type*.—Herbaceous Perennial.

*Plant habit*.—Bushy upright plant habit with stems that do not lodge.

*Height and spread*.—In-ground trial plants 3 years in age; 105 cm in height and 95 cm in width, in-ground trial plants 5 years in age; 107 cm in height and 105 cm in width.

*Hardiness*.—U.S.D.A. Zones 4 to 8.

*Diseases and pests*.—Highly resistant to rust (*Coleosporium* sp.) and powdery mildew (*Golovinomyces* sp.), no susceptibility or resistance to pests has been observed.

*Root description*.—Fine, 155A in color.

*Propagation*.—Shoot tip cuttings.

*Growth rate*.—Vigorous.

*Root development*.—Cuttings initiate roots within three to four weeks and are fully rooted and removed from mist by six weeks, a rooted cutting can be potted up to a quart or one-gallon pot the first year, and will produce 1 to 3 blooming stems the following year.

Stem description:

*Shape*.—Round.

*Stem color*.—A blend of 145A, N144A to N144B, leaf scars 200A.

*Stem size*.—An average of 105 cm in length and an average of 6 mm in diameter.

*Stem surface*.—Glossy, smooth with linear ridges, leaf scars are present; an average of 4 scars per linear cm.

*Stem number*.—One-year old, container-grown plants produced 1-3 stems, two-year old, in-ground plants produced an average of nine stems, and three year old, in-ground plants produced an average of 50 stems.

*Stem aspect*.—Held upright.

*Stem branching*.—Un-branched.

Foliage description:

*Leaf division*.—Simple.

*Leaf arrangement*.—Alternate, sometimes opposite.

*Leaf shape*.—Linear.

*Leaf size*.—Up to 11 cm in length and 3 mm in width.

*Leaf number*.—Average of 73 per stem.

*Leaf base*.—Acute.

*Leaf apex*.—Acuminate.

*Leaf margin*.—Very finely denticulate, teeth spread an average of 3 mm apart.

*Leaf venation*.—Pinnate, color matches leaf color except the lower one quarter of the mid rib is145B on both surfaces.

*Leaf surface*.—Both surfaces glabrous and dull.

*Internode length*.—Average of 5 mm.

*Leaf color*.—Young and mature upper and lower surfaces; N138A and 146A with no anthocyanin coloration when grown in full sun.

*Leaf attachment*.—Sessile to stem.

*Petioles*.—None.

Inflorescence description:

*Inflorescence type*.—Capitula organized in a compound corymbiform array.

*Inflorescence number*.—1 per stem.

*Inflorescence fragrance*.—None.

*Inflorescence size*.—Average of 18 cm in depth and 16 cm in diameter with the capitula 1.5 cm in depth and 1.2 in diameter.

*Peduncles*.—Round in shape, up to 2.5 cm in length and 1 mm in diameter, surface is dull and glabrous, color is 146A.

*Pedicels*.—Round in shape, up to 1.8 cm in length and 1 mm in diameter, surface is dull and glabrous, color is 146A.

*Phyllaries*.—Up to 50 per capitulum, discoid head, acuminate apex, entire margins, bluntly acute base, bracts linear in shape, up to 3 mm in length and 1 mm in width, color of outer and inner surfaces; tip is 83A,147B in color with tips 83A, curved outward in aspect (not appressed to the capitula).

*Flower buds*.—Linear in shape, slightly glossy overall appearance, average of 5 mm in length and 2 mm in width, color; 144A and 144B with tips 187A.

*Flower longevity*.—Average of 3 to 5 days per floret, depending on temperature.

*Flower type*.—Discoid florets, no ray florets.

*Florets quantity*.—Average of 16 per capitulum.

*Florets*.—1 cm in depth, 4 mm in width, elongated tube in shape and flat on top, base 143A, mid section a blend of 145A and 143A, tips towards the top N92A.

*Petals*.—5 petals, 55% of petals fused, free top portion; base to mid section is linear in shape, un-fused portion of petals drop into downward and inward hanging angles and slightly curl under, tube is 7 mm in length and 1 mm in width, loose petals at top are 4 mm in length and 1 mm in width, petal tips acute in shape, inner and outer surfaces are glabrous, slightly velvety, shiny, entire margins, base fused to tube, color; N82A, tips 83A, base 84C and 84D.

*Pistils*.—1 per floret, bi-fid stigma, 83A in color, 3 mm in length and 4 mm in width, style 5 mm in length and <0.5 mm in width, a blend of 68A and 72A in color, ovary is 5 mm in length and 4 mm in width and oval in shape, NN155A in color, pappus bristles at base, 5 mm in length, 183A in color.

*Stamens*.—5 per floret, filaments very fine, 4 mm in length, translucent, color; NN155A, anthers; 2 mm in length and 1 mm in width, base 71A, center NN155A, tip 79A, pollen abundant in quantity and NN155A in color.

*Fruit/seeds*.—Fruit and seed production has not been observed.

It is claimed:

1. A new and distinct variety of *Vernonia* plant designated 'Summer's End' as described and illustrated herein.

* * * * *